US010184096B2

(12) United States Patent
Fernandez-Prieto et al.

(10) Patent No.: US 10,184,096 B2
(45) Date of Patent: Jan. 22, 2019

(54) UREA GELLANT

(71) Applicant: The Procter & Gamble Company, Cincinnati, OH (US)

(72) Inventors: Susana Fernandez-Prieto, Benicarlo-Castellon (ES); Juan Miravet-Celades, Castellon (ES); Juan-Jose Ojeda-Flores, Castellon (ES); Johan Smets, Lubbeek (BE)

(73) Assignee: The Procter & Gamble Company, Cincinnato, OH (US)

( * ) Notice: Subject to any disclaimer, the term of this patent is extended or adjusted under 35 U.S.C. 154(b) by 104 days.

(21) Appl. No.: 15/187,819

(22) Filed: Jun. 21, 2016

(65) Prior Publication Data

US 2016/0369208 A1 Dec. 22, 2016

(30) Foreign Application Priority Data

Jun. 22, 2015 (EP) ..................................... 15173059

(51) Int. Cl.
*C11D 3/32* (2006.01)
*C11D 1/00* (2006.01)
*C11D 3/26* (2006.01)
*C07D 213/40* (2006.01)
*C11D 7/32* (2006.01)
*C11D 1/22* (2006.01)

(52) U.S. Cl.
CPC ............ *C11D 3/323* (2013.01); *C07D 213/40* (2013.01); *C11D 1/00* (2013.01); *C11D 1/22* (2013.01); *C11D 3/26* (2013.01); *C11D 3/32* (2013.01); *C11D 7/3272* (2013.01)

(58) Field of Classification Search
CPC ................ C11D 1/00; C11D 3/26; C11D 3/32
USPC ........................................ 510/499, 500, 501
See application file for complete search history.

(56) References Cited

U.S. PATENT DOCUMENTS

| 3,929,678 | A | 12/1975 | Laughlin et al. |
| 8,236,748 | B2 | 8/2012 | Fernandez Prieto et al. |
| 8,309,507 | B2 | 11/2012 | Fernandez Prieto et al. |
| 8,668,918 | B2 | 3/2014 | Hong et al. |
| 9,115,164 | B2 | 8/2015 | Yamanaka et al. |
| 2014/0005279 | A1* | 1/2014 | Yamanaka ............ C07C 275/34 514/777 |

FOREIGN PATENT DOCUMENTS

DE 19749979 * 5/1999

OTHER PUBLICATIONS

English language machine translation of DE19749979, (Abstract, claims, specification).*
Bianca K. Verlinden a, Mama De Beer'"Boobalan Pachaiyappan'" Ethan Besaans ;:, Warren A. Andayi ;'Janette Reader;:, Jandeli Niemand , Riette Van Biljon;:, Kiplin Guy', Timothy Egan \ Patrick M. Woster , Lyn-Marie Birkholtz; Interrogating alkyl and arylal-lkylpolyamino (bis )urea and (bis) thiourea isosteres as potent antimalarial chemotypes against multiple lifecycle forms of *Plasmodium falciparum* parasites, Bioorganic & Medicinal Chemistry 23, 2015, pp. 5131-5143.
Nagendar Pendem, Celine Douat, Paul Claudon, Michel Laguerre, Sabine Castano, Bernard Desbat, Dominique Cavagnat, Eric Ennifar, Brice Kauffinann and Gilles Guichard, Helix-Forming Propensity of Aliphatic Urea Oligomers Incorporating Noncanonical Residue Substitution Patterns, Journal of the American Chemical Society, *J. Am. Chem. Soc.* 2013, 135,4884-4892.
Tadashi Endo, Akihiro Okubo, Yuji Kaneko, Masatoshi Uehara, Hidetoshi Tasai, Akiyoshi Sato, Kunio Nikki, Naoya Nakagawa,and Shinichi Kame, Methylation of a Benzene Ring as a Chemical Signal. Marked Changes in the Pattern of Temperature Dependence of the Selectivity in Oxidation of a Pair of Associating Thiols, © 1982 *The Chemical Society if Japan Bull. Chem. Soc. Jpn.*, 55, 2224-2232 (1982) [vol. 55, No. 7].
Nagendar Pendem, Yella Reddy Nelli, Celine Douat, Lucile Fischer, Michel Lagurre, Eric Ennifar, Brice Kauffmann, and Gilles Guichard, Controlling Helix Formation in the γ-Peptide Superfamily: Heterogeneous Foldamers with Ureal/Amide and Ureal/Carbamate Backbones; Angew. Chern. Int. Ed. 2013,52,4147-4151.
Fabrizio Ribaudo, Piet W.N.M. Van Leeuwen, and Joost N.H. Reek, Phosphorus Functionalized Dendrimers and Hyperbranched Polymers: Is There a Need for Perfect Dendrimers in Catalysis?; Israel Journal of Chemistry vol. 49 2009 pp. 79-98.
Malgorzata N. Drwal . Keli Agama . Yves Pommier, ' Renate Griffith, Development of purely structure-based pharmacophores for the topoisomerase I-DNA-ligand binding pocket; J Comput Aided Mol Des (2013) 27: pp. 1037-1049.
Gareth O. Lloyd, Marc-Oliver M. Piepenbrock, Jonathan A. Foster, Nigel Clarke and Jonathan W. Steed, Anion tuning of chiral bis(urea) low molecular weight gels; The Royal Society of Chemistry 2012, Soft Matter, 2012 vol. 8, pp. 204-216.
Shiv K. Sharma, Yu \Vu, Nora Steinbergs, Michael L Crowley, Allison S. Hanson, Robert A, Casero, Jr., and Patrick M. Woster, (Bis)urea and (Bis)thiourea Inhibitors of Lysine-Specific Demethylase 1 as Epigenetic Modulators, Journal of Medicinal Chemistry, 2010, 53, pp. 5197-5212.
European Search Report for Application No. 15173059.5-1451, dated Dec. 4, 2015, 10 pages.

* cited by examiner

*Primary Examiner* — Gregory R Delcotto
(74) *Attorney, Agent, or Firm* — Andres Velarde

(57) ABSTRACT

Urea gellants that are suitable for use in liquid compositions. Liquid compositions that include urea gellants. Related processes.

2 Claims, No Drawings

UREA GELLANT

FIELD OF THE INVENTION

The present invention relates to structurants that are easy to fabricate, and can even be fabricated in-situ, in the product.

BACKGROUND OF THE INVENTION

It has long been desired to formulate a broad range of variants, offering unique benefits, from a single base detergent composition. By adding specific benefit agents to such a base, one could simply and cost-effectively provide compositions that are tailored to a specific group of users. However, a major challenge is to find structurants to thicken such compositions which are compatible with a broad range of potential detergent ingredients.

Amido-gellants, such as those disclosed in WO2011/112887 and WO2011/112910 have been discovered to be compatible with a broad range of detergent ingredients, including enzymes. However, amido-gellants can require complex chemistry in order to make them. Also, since structurants increase viscosity, they can be difficult to incorporate homogeneously into a liquid composition.

Hence, a need remains for a structurant which is easy to fabricate, and also easy to blend into liquid compositions, especially liquid detergent compositions.

SUMMARY OF THE INVENTION

The present invention relates to urea gellants having the following formula:

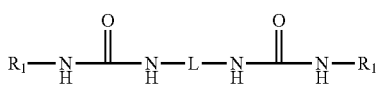
[I]

wherein: $R_1$ is an end-group comprising an aromatic ring, and L is a linking moiety of molecular weight from 28 to 350 g/mol, and with the exclusion that the urea gellant is not a protein, liquid detergent compositions comprising a surfactant and such urea gellants, processes for structuring liquid compositions, and the use of such urea gellants for structuring liquid compositions.

DETAILED DESCRIPTION OF THE INVENTION

Urea gellants can be fabricated using a simplified reaction procedure to other amido-gellants, and can even be made in-situ in the liquid composition to be structured. As such, they offer a means of providing a structurant whose constituent parts can be readily dispersed in the liquid composition, and then combined to provide the desired structuring. The urea gellants are also able to structure both aqueous and non-aqueous liquid compositions.

All percentages, ratios and proportions used herein are by weight percent of the composition, unless otherwise specified. All average values are calculated "by weight" of the composition or components thereof, unless otherwise expressly indicated.

External Structurant:

The external structurant preferably imparts a shear thinning viscosity profile to the liquid composition, independently from, or extrinsic from, any structuring effect of detersive surfactants which may be present in the composition. Preferred external structurants include those which provide a pouring viscosity from 50 cps to 20,000 cps, more preferably from 200 cps to 10,000 cps, most preferably from 500 cps to 7,000 cps. The liquid compositions, especially liquid detergent compositions, preferably have a resting viscosity of at least 1,500 cps, preferably at least 10,000 cps, more preferably at least 50,000 cps. This resting (low stress) viscosity represents the viscosity of the liquid composition under gentle shaking in the package and during transportation, and also results in stable suspension of insoluble actives, such as microcapsules, silicone droplets, particulates, and the like. Alternatively, the liquid composition may be a thixotropic gel. Such compositions may have a resting viscosity of from 10,000 cps to 500,000 cps, preferably from 100,000 cps to 400,000 cps, more preferably from 200,000 to 300,000. The preferred shear-thinning characteristics of the liquid composition is defined as a ratio of low stress viscosity to pouring viscosity of at least 2, preferably at least 10, more preferably at least 100, up to 2000.

The pouring viscosity is measured at a shear rate of 20 sec-1, which is a shear rate that the liquid composition is typically exposed to during pouring. The resting (low stress) viscosity is determined under a constant stress of 0.1 Pa during a viscosity creep experiment over a 5 minute interval. Rheology measurements over the 5 minute interval are made after the composition has has rested at zero shear rate for at least 10 minutes, between loading the sample in the rheometer and running the test. The data over the last 3 minutes are used to fit a straight line, and from the slope of this line, the low stress viscosity is calculated. The viscosity is measured at 21° C. using a TA AR 2000 (or AR G2) rheometer with a 40 mm stainless steel plate having a gap of 500 microns.

Urea Gellant

The liquid composition includes a urea gellant as an external structurant at a level from 0.01 wt % to 10 wt %, preferably from 0.05 wt % to 5 wt %, more preferably from 0.1 wt % to 2 wt %, most preferably from 0.1 wt % to 1 wt %. In an alternative embodiment, the liquid composition comprises from 0.1 wt % to 0.5 wt % of the urea gellant.

The urea gellant comprises at least two urea groups. The urea gellant has the following formula:

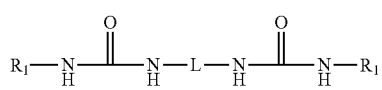
[I]

wherein: $R_1$ is an end-group comprising an aromatic ring, and L is a linking moiety of molecular weight from 140 to 350 g/mol, and with the exclusion that the urea gellant is not a protein. It is believed that the presence of the aromatic rings improves the ability of the urea gellants to organise in the liquid composition, in order to improve structuring. The urea gellant comprises two $R_1$ groups. The $R_1$ groups can be the same or different. Preferably, the $R_1$ groups are the same. Preferably, the urea gellant is symmetric.

In one embodiment, L is an aliphatic linking group with a backbone chain of from 2 to 18, preferably 10 to 18 carbon atoms, preferably —$(CH_2)_n$— wherein n is selected from 2 to 18, preferably 10 to 18.

Alternatively, L can comprise at least 2 substituted or unsubstituted aromatic rings. Preferably, L is:

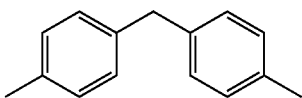

R$_1$ can be

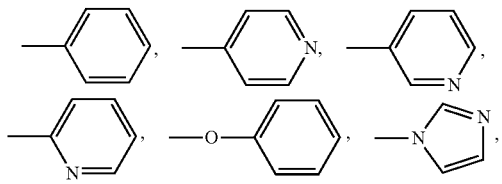

or

-L'-R or R, and combinations thereof.

More preferably, R$_1$ is -L'-R.

L' can be an aliphatic linking group with a substituted or unsubstituted backbone chain of from 1 to 10 carbon atoms. Preferably, L' is —(CH$_2$)$_n$— wherein n is selected from 1 to 10, or from 1 to 5.

When L is an aliphatic linking group with a backbone chain of from 10 to 18 carbon atoms, L' is an aliphatic linking group with a, preferably unsubstituted, backbone chain of from 1 to 10 carbon atoms, preferably —(CH$_2$)$_n$— wherein n is selected from 1 to 10.

When L comprises at least 2 substituted or unsubstituted aromatic rings, L' is preferably an aliphatic linking group with a substituted or unsubstituted backbone chain of from 1 to 10 carbon atoms, preferably —(CH$_2$)$_n$— wherein n is selected from 1 to 5.

R is selected from the group consisting of:

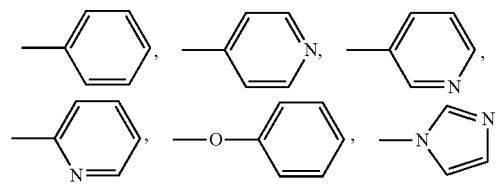

The urea gellant preferably has a molecular weight from 280 to 800 g/mol, preferably 400 to 600 g/mol. Without being bound by theory, we believe that urea gellants having a molecular weight of below 280 g/mol gel less effectively, due to their higher solubility, while a molecular weight of greater than 800 g/mol leads to increased precipitation of the urea gellant, instead of assembly of the molecule. Surprisingly, it has been found that urea gellants, having a molecular weight of greater than 800 g/mol, are effective at structuring detergent compositions having a high surfactant concentration. It is believed that micellisation at the high surfactant concentration improves the solubility of even urea gellants of molecular weight above 800 g/mol. By high surfactant concentration, it is meant that the surfactant concentration is greater than 30 wt %, preferably greater than 40 wt %, more preferably greater than 60 wt %.

The urea gellant preferably has a minimum gelling concentration (MGC) of from 0.1 to 100 mg/mL in the liquid composition, preferably from 0.1 to 50 mg/mL, more preferred from 0.5 to 30 mg/mL in accordance with the MGC Test Method. The MGC as used herein can be represented as mg/ml or as a wt %, where wt % is calculated as the MGC in mg/ml divided by 10. In one embodiment, when measured in the liquid composition, the MGC is from 0.1 to 100 mg/mL, preferably from 0.1 to 50 mg/mL of said urea gellant, more preferably from 0.5 to 30 mg/mL, or at least 0.1 mg/mL, at least 0.3 mg/mL, at least 0.5 mg/mL, at least 1.0 mg/mL, at least 2.0 mg/mL of urea gellant. While liquid compositions may comprise a urea gellant structurant at a concentration either above or below the MGC, the urea gellants of the invention result in particularly useful rheologies below the MGC.

Suitable urea gellants may be selected from the group consisting of: 1,1'-(decane-1,10-diyl)bis(3-(pyridin-4-ylmethyl)urea); 1,1'-(undecane-1,11-diyl)bis(3-(pyridin-4-ylmethyl)urea); 1,1'-(dodecane-1,12-diyl)bis(3-(pyridin-4-ylmethyl)urea); 1,1'-(decane-1,10-diyl)bis(3-(pyridin-3-ylmethyl)urea); 1,1'-(undecane-1,11-diyl)bis(3-(pyridin-3-ylmethyl)urea); 1,1'-(dodecane-1,12-diyl)bis(3-(pyridin-3-ylmethyl)urea); 1,1'-(decane-1,10-diyl)bis(3-(pyridin-2-ylmethyl)urea); 1,1'-(undecane-1,11-diyl)bis(3-(pyridin-2-ylmethyl)urea); 1,1'-(dodecane-1,12-diyl)bis(3-(pyridin-2-ylmethyl)urea); 1,1'-(decane-1,10-diyl)bis(3-(3-(1H-imidazol-1-yl)propyl)urea); 1,1'-(undecane-1,11-diyl)bis(3-(3-(1H-imidazol-1-yl)propyl)urea); 1,1'-(dodecane-1,12-diyl)bis(3-(3-(1H-imidazol-1-yl)propyl)urea); 1,1'-(decane-1,10-diyl)bis(3-(2-(pyridin-4-yl)ethyl)urea); 1,1'-(undecane-1,11-diyl)bis(3-(2-(pyridin-4-yl)ethyl)urea); 1,1'-(dodecane-1,12-diyl)bis(3-(2-(pyridin-4-yl)ethyl)urea); 1,1'-(decane-1,10-diyl)bis(3-(2-(pyridin-3-yl)ethyl)urea); 1,1'-(undecane-1,11-diyl)bis(3-(2-(pyridin-3-yl)ethyl)urea); 1,1'-(dodecane-1,12-diyl)bis(3-(2-(pyridin-3-yl)ethyl)urea); 1,1'-(decane-1,10-diyl)bis(3-(2-(pyridin-2-yl)ethyl)urea); 1,1'-(undecane-1,11-diyl)bis(3-(2-(pyridin-2-yl)ethyl)urea); 1,1'-(dodecane-1,12-diyl)bis(3-(2-(pyridin-2-yl)ethyl)urea); 1,1'-(methylenebis(4,1-phenylene))bis(3-(2-(pyridin-2-yl)ethyl)urea); 1,1'-(methylenebis(4,1-phenylene))bis(3-(2-(pyridin-3-yl)ethyl)urea); 1,1'-(methylenebis(4,1-phenylene))bis(3-(2-(pyridin-4-yl)ethyl)urea); 1,1'-(methylenebis(4,1-phenylene))bis(3-(pyridin-4-ylmethyl)urea); 1,1'-(methylenebis(4,1-phenylene))bis(3-(pyridin-3-ylmethyl)urea); 1,1'-(methylenebis(4,1-phenylene))bis(3-(pyridin-2-ylmethyl)urea) and mixtures of thereof.

More preferably, the urea gellants is selected from the group consisting of: 1,1'-(dodecane-1,12-diyl)bis(3-(pyridin-4-ylmethyl)urea); 1,1'-(dodecane-1,12-diyl)bis(3-(pyridin-3-ylmethyl)urea); 1,1'-(dodecane-1,12-diyl)bis(3-(pyridin-2-ylmethyl)urea); 1,1'-(dodecane-1,12-diyl)bis(3-(2-(pyridin-4-yl)ethyl)urea); 1,1'-(dodecane-1,12-diyl)bis(3-(2-(pyridin-2-yl)ethyl)urea); 1,1'-(methylenebis(4,1-phenylene))bis(3-(2-(pyridin-2-yl)ethyl)urea); 1,1'-(methylenebis(4,1-phenylene))bis(3-(pyridin-4-ylmethyl)urea); 1,1'-(methylenebis(4,1-phenylene))bis(3-(pyridin-3-ylmethyl)urea); 1,1'-(methylenebis(4,1-phenylene))bis(3-(pyridin-2-ylmethyl)urea) and mixtures of thereof.

1,1'-(dodecane-1,12-diyl)bis(3-(pyridin-4-ylmethyl)urea) is the most preferred urea gellant.

To provide more robust structuring, the liquid composition may comprise a mixture of two or more urea gellant structurants. Such a mixture may include a urea gellant structurant which has higher solubility in water and/or non-aminofunctional solvents, with a urea gellant with lower solubility in water and/or non-aminofunctional solvents. Without intending to be bound by theory, it is believed that a urea gellant that is more soluble in water may have difficulty forming a gel in a cleaning composition at a low level, while one that is less soluble, may have difficulty forming a gel because it will be difficult to solubilize it.

Liquid Composition

The urea gellants can be used for structuring liquid compositions. Preferred liquid compositions are "consumer product" compositions, such as baby care, beauty care, fabric & home care, family care, feminine care, health care, and the like. Such products include but are not limited to lotions for wipes; hair treatment products (human, dog, and/or cat), including, bleach, colouring agents, hair conditioners, shampoos, and the like; deodorants and antiperspirants; personal cleansing; cosmetics; skin care creams, skin lotions, and other topically applied products; shaving products; products for treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; and oral care products including toothpastes, tooth gels, tooth rinses, denture adhesives, tooth whiteners.

The amido gellants are particularly useful for liquid compositions which are easily flowable or gels which initially pile up upon pouring.

In particular, the urea gellants can be used for structuring liquid detergent compositions. Liquid detergent compositions as described herein include but are not limited to consumer products such as: shampoos; skin cleaners and exfolients; shaving liquids, foams and gels; products for treating fabrics, hard surfaces and any other surfaces in the area of fabric and home care, including: dishwashing, laundry cleaning, laundry and rinse additives, hard surface cleaning including floor and toilet bowl cleaners.

Laundry detergent compositions are particularly preferred. As used herein, "laundry detergent composition" refers to any composition capable of cleaning a fabric, or providing a fabric care benefit, e.g., on clothing, in a domestic washing machine. Laundry detergent compositions are typically added to the wash cycle during machine washing of fabrics.

The liquid composition can include solids or gases in suitably subdivided form, but the overall composition excludes product forms which are non-liquid overall, such as tablets or granules. The liquid compositions preferably have densities in the range from of 0.9 to 1.3 grams per cubic centimeter, more preferably from 1.00 to 1.10 grams per cubic centimeter, excluding any solid additives but including any bubbles, if present.

Liquid detergent compositions comprise at least one detersive surfactant. The liquid detergent compositions of the present invention may comprise from 1% to 70%, preferably from 5% to 60%, more preferably from 10% to 50%, most preferably from 15% to 45% by weight of a surfactant selected from the group consisting of: anionic, nonionic surfactants and mixtures thereof. The preferred weight ratio of anionic to nonionic surfactant is from 100:0 (i.e. no nonionic surfactant) to 5:95, more preferably from 99:1 to 1:4, most preferably from 5:1 to 1.5:1.

The liquid detergent compositions of the present invention preferably comprise from 1 to 50%, more preferably from 5 to 40%, most preferably from 10 to 30% by weight of one or more anionic surfactants. Preferred anionic surfactant are selected from the group consisting of: C11-C18 alkyl benzene sulphonates, C10-C20 branched-chain and random alkyl sulphates, C10-C18 alkyl ethoxy sulphates, mid-chain branched alkyl sulphates, mid-chain branched alkyl alkoxy sulphates, C10-C18 alkyl alkoxy carboxylates comprising 1-5 ethoxy units, modified alkylbenzene sulphonate, C12-C20 methyl ester sulphonate, C10-C18 alpha-olefin sulphonate, C6-C20 sulphosuccinates, and mixtures thereof. However, by nature, every anionic surfactant known in the art of detergent compositions may be used, such as those disclosed in "Surfactant Science Series", Vol. 7, edited by W. M. Linfield, Marcel Dekker. The liquid detergent compositions preferably comprise at least one sulphonic acid surfactant, such as a linear alkyl benzene sulphonic acid, or the water-soluble salt form of the acid.

The liquid detergent compositions of the present invention preferably comprise up to 30%, more preferably from 1 to 15%, most preferably from 2 to 10% by weight of one or more nonionic surfactants. Suitable nonionic surfactants include, but are not limited to C12-C18 alkyl ethoxylates ("AE") including the so-called narrow peaked alkyl ethoxylates, C6-C12 alkyl phenol alkoxylates (especially ethoxylates and mixed ethoxy/propoxy), block alkylene oxide condensate of C6-C12 alkyl phenols, alkylene oxide condensates of C8-C22 alkanols and ethylene oxide/propylene oxide block polymers (Pluronic®-BASF Corp.), as well as semi polar nonionics (e.g., amine oxides and phosphine oxides). An extensive disclosure of suitable nonionic surfactants can be found in U.S. Pat. No. 3,929,678.

The liquid compositions may be opaque, semi-transparent or even clear. When clarity of the liquid composition is desired, the liquid composition has a turbidity of from 5 NTU to less than 3000 NTU, preferably less than 1000 NTU, more preferably less than 500 NTU and most preferably less than 100 NTU.

The liquid composition of the present invention may also comprise from 2% to 40%, more preferably from 5% to 25% by weight of a non-aminofunctional organic solvent. Non-aminofunctional organic solvents are organic solvents which contain no amino functional groups. Preferred non-aminofunctional organic solvents include monohydric alcohols, dihydric alcohols, polyhydric alcohols, glycerol, glycols including polyalkylene glycols such as polyethylene glycol, and mixtures thereof. More preferred non-aminofunctional organic solvents include monohydric alcohols, dihydric alcohols, polyhydric alcohols, glycerol, and mixtures thereof. Highly preferred are mixtures of non-aminofunctional organic solvents, especially mixtures of two or more of the following: lower aliphatic alcohols such as ethanol, propanol, butanol, isopropanol; diols such as 1,2-propanediol or 1,3-propanediol; and glycerol. Also preferred are mixtures of propanediol and diethylene glycol. Such mixtures preferably contain no methanol or ethanol.

Preferable non-aminofunctional organic solvents are liquid at ambient temperature and pressure (i.e. 21° C. and 1 atmosphere), and comprise carbon, hydrogen and oxygen. Non-aminofunctional organic solvents may be present when preparing a premix, or in the final liquid composition.

The urea gellants are especially suited for liquid composition to be encapsulated in a water soluble film, to form a unit dose article, since there are effective in low water or even nil-water liquid compositions. Such unit dose articles comprise a liquid composition of the present invention, wherein the liquid composition comprises less than 20%, preferably less than 15%, more preferably less than 10% by weight of water, and the liquid composition is enclosed in a water-soluble or dispersible film. Such unit-dose articles can be formed using any means known in the art. Unit dose articles comprising a laundry detergent composition are particularly preferred.

Suitable water soluble pouch materials include polymers, copolymers or derivatives thereof. Preferred polymers, copolymers or derivatives thereof are selected from the group consisting of: polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof.

Since the liquid compositions and unit dose articles, of the present invention, maintain their colour over longer periods of time, they can be packaged within transparent or translucent containers, while maintaining an aesthetically pleasing appearance. Translucent containers are containers having sufficient transparency, that the colour of the contained composition or unit dose articles can be seen.

The urea gellants can be processed in different ways, preferably using a trigger in order to drive the self-assembling of the molecules and form a structured product.

Temperature can be used as trigger: the urea gellant can be added to the product to be structured, heat is applied until the gellant is dissolved and then the structure is formed through cooling. However, thermal processes are more challenging on large scales. As such, pH can be used as trigger, when the urea gellant comprises at least one pH sensitive group, since the solubility of the urea gellant is higher in its ionic form and lower in its neutral form. Urea gellants which comprise at least one pH sensitive group can be processed as follows:

a. the urea gellant is preferably dissolved to form a premix. Urea gellants having a pyridine group, are readily dissolved in acid premixes, while urea gellants containing an acid group, can be readily dissolved in basic premixes.

b. the urea gellant premix is added to the composition c. the pH is adjusted by adding at appropriate pH adjustment agent, as is known in the art. Alternatively, urea gellants can also be produced in-situ. This method has several advantages, such as fast preparation of urea gellants and simplified incorporation into the final composition.

A suitable process for in-situ structuring of a liquid composition, using a urea gellant can comprise the steps of:

(i) providing a solvent premix comprising a solvent, preferably selected from the group consisting of: water, a C1-C18 alcohol, and mixtures thereof;

(ii) adding an amine-precursor and isocyanate-precursor to the solvent premix;

(iii) heating the solvent premix to from 20° C. to 60° C.; and (iv) adding the solvent premix to a liquid composition.

Test Methods:

1. Turbidity (NTU):

The turbidity (measured in NTU: Nephelometric Turbidity Units) is measured using a Hach 2100P turbidity meter calibrated according to the procedure provided by the manufacture.

The sample vials are filled with 15 ml of representative sample and capped and cleaned according to the operating instructions. If necessary, the samples are degassed to remove any bubbles either by applying a vacuum or using an ultrasonic bath (see operating manual for procedure). The turbidity is measured using the automatic range selection.

2. Minimum Gelling Concentration (MGC)

MGC is calculated by a tube inversion method based on R. G. Weiss, P. Terech; "Molecular Gels: Materials with self-assembled fibrillar structures" 2006 springer, p 243. In order to determine the MGC, three screenings are done:

a) First screening: prepare several vials increasing the urea gellant concentration from 0.5% to 5.0 weight % in 0.5% steps b) Determine in which interval the gel is formed (one inverted sample still flowing and the next one is already a strong gel). In case no gel is formed at 5%, higher concentrations are used.

c) Second screening: prepare several vials increasing the urea gellant concentration in 0.1 weight % steps in the interval determined in the first screening.

d) Determine in which interval the gel is formed (one inverted sample still flowing and the next one is already a strong gel)

e) Third screening: in order to have a very precise percentage of the MGC, run a third screening in 0.025 weight % steps in the interval determined in the second screening.

f) The Minimum Gelling Concentration (MGC) is the lowest concentration which forms a gel in the third screening (does not flow on inversion of the sample).

For each screening, samples are prepared and treated as follows: 8 mL vials (Borosilacate glass with Teflon cap, ref. B7857D, Fisher Scientific Bioblock) are filled with 2.0000±0.0005 g (KERN ALJ 120-4 analytical balance with ±0.1 mg precision) of the liquid (comprising the liquid composition and urea gellant) for which we want to determine the MGC. The vial is sealed with the screw cap and left for 10 minutes in an ultrasound bath (Elma Trans sonic T 710 DH, 40 kHz, 9.5 L, at 25° C. and operating at 100% power) in order to disperse the solid in the liquid. Complete dissolution is then achieved by heating, using a heating gun (Bosch PHG-2), and gentle mechanical stirring of the vials. It is crucial to observe a completely clear solution. Handle vials with care. While they are manufactured to resist high temperatures, a high solvent pressure may cause the vials to explode. Vials are cooled to 25° C., for 10 min in a thermostatic bath (Compatible Control Thermostats with controller CC2, D77656, Huber). Vials are inverted, left inverted for 1 minute, and then observed for which samples do not flow. After the third screening, the concentration of the sample that does not flow after this time is the MGC. For those skilled in the art, it is obvious that during heating solvent vapours may be formed, and upon cooling down the samples, these vapours can condense on top of the gel. When the vial is inverted, this condensed vapour will flow. This is discounted during the observation period. If no gels are obtained in the concentration interval, higher concentrations must be evaluated.

3. Rheology

An AR-G2 rheometer from TA Instruments is used for rheological measurements. Plate: 40 mm standard steel parallel plate, 300 μm gap.

1. Gel strength: The gel strength is measured using a stress sweep test whereby the oscillation stress is increased from 0.001 Pa to 10 Pa, taking 10 points per decade at 20° C. and at a frequency of 1 Hz. We use G' and G" within the linear viscoelastic region and the oscillation stress at the point where G' and G" cross over as a measure for the gel strength, as shown in FIG. 1.

EXAMPLES

Example 1: Synthesis of 1,1'-(dodecane-1,12-diyl)bis(3-(pyridin-4-ylmethyl)urea)

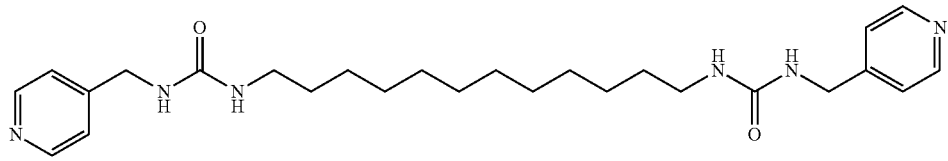 [SMILES: O=C(NCCCCCCCCCCCCNC(=O)NCc1ccncc1)NCc1ccncc1]

1,12-Diisocyanatodocane (2 gr, 7.93 mmol) is stirred in dry acetonitrile (130 mL). A solution of 4-aminomethyl pyridine (1.8 mL, 17.58 mmol) in dry acetonitrile (60 mL) is added drop wise. The mixture is stirred at 50° C. overnight. Solvent is removed with reduced pressure and a white solid is obtained. The solid is washed three times with 100 mL of a solution of 0.5% NaHCO$_3$ in weight and finally washed with distilled water. 1,1'-(dodecane-1,12-diyl)bis(3-(pyridin-4-ylmethyl)urea) compound is dried two days at 70° C.

Example 2: Synthesis of 1,1'-(methylenebis(4,1-phenylene))bis(3-(pyridin-2-ylmethyl)urea)

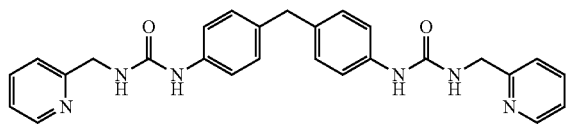 [SMILES: O=C(NCc1ccccn1)Nc1ccc(Cc2ccc(NC(=O)NCc3ccccn3)cc2)cc1]

4,4'-Methylenebis(phenyl isocyanate) (2 gr, 7.99 mmol) is stirred in dry acetonitrile (130 mL). A solution of 2-aminomethyl pyridine (1.8 mL, 17.58 mmol) in dry acetonitrile (60 mL) is added drop wise. The mixture is stirred at 50° C. overnight. Solvent is removed with reduced pressure and a white solid is obtained. The solid is washed three times with a solution of NaHCO$_3$ (0.5% wt) (100 ml×3) and finally washed with distilled water. 1,1'-(methylenebis(4,1-phenylene))bis(3-(pyridin-2-ylmethyl)urea) compound is dried two days at 70° C.

Example 3: Liquid Laundry Detergent Compositions Comprising a Urea Gellant

An unstructured liquid detergent composition was prepared by blending the following ingredients together in the proportions below, to provide Composition A:

| Composition A | wt % |
| --- | --- |
| C10-16-alkylbenzenesulfonic Acid | 12.5 |
| C14-15 ethoxylated Alcohols | 9.6 |
| 2-methyl-1,3-propanediol | 1 |
| Diethylene glycol | 1.5 |
| Citric acid | 4 |
| Sodium cumene sulfonate | 2 |
| Monoethanolamine borate | 4 |
| C12-18 Fatty acids | 4 |
| Diethylenediaminepenta(methyl phosphonic) acid | 0.3 |
| Ethoxy sulphated hexamethylene diamine quaternized | 1.9 |
| minors (silicone, dye, . . .) | up to 1% |
| Sodium hydroxide | to pH 8 |
| Water | up to 100% |

The minimum gelling concentration (MGC) was measured for the below urea gellants, using composition A:

| IUPAC NAME | STRUCTURE | MGC (% w/w) |
| --- | --- | --- |
| 1,1'-(octane-1,8-diyl)bis(3-(pyridin-4-ylmethyl)urea) | 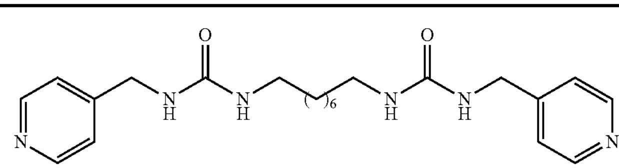 | 0.9 |
| 1,1'-(dodecane-1,12-diyl)bis(3-(pyridin-4-ylmethyl)urea) | 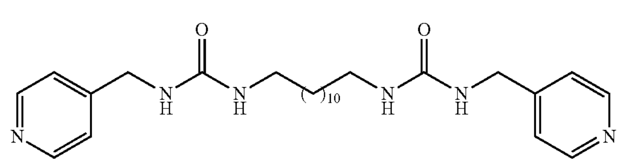 | 0.25 |

| IUPAC NAME | STRUCTURE | MGC (% w/w) |
|---|---|---|
| 1,1'-(dodecane-1,12-diyl)bis(3-(pyridin-3-ylmethyl)urea) | 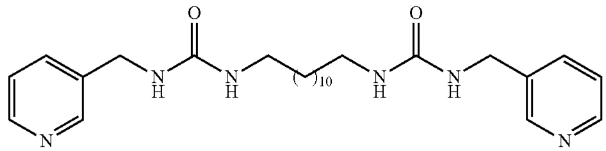 | 1.3 |
| 1,1'-(dodecane-1,12-diyl)bis(3-(pyridin-2-ylmethyl)urea) | 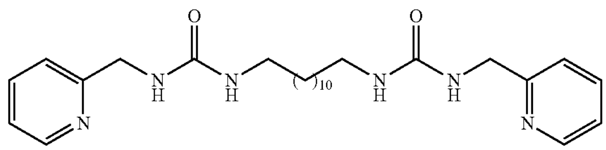 | 1 |
| 1,1'-(dodecane-1,12-diyl)bis(3-(2-(pyridin-4-yl)ethyl)urea) | 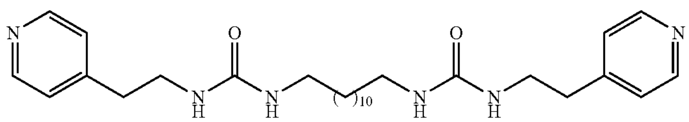 | 0.6 |
| 1,1'-(methylenebis(4,1-phenylene))bis(3-(pyridin-4-ylmethyl)urea) | 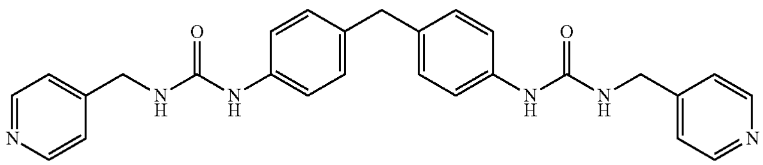 [SMILES: O=C(NCc1ccncc1)Nc1ccc(Cc2ccc(NC(=O)NCc3ccncc3)cc2)cc1] | 1.5 |
| 1,1'-(methylenebis(4,1-phenylene))bis(3-(pyridin-3-ylmethyl)urea) | 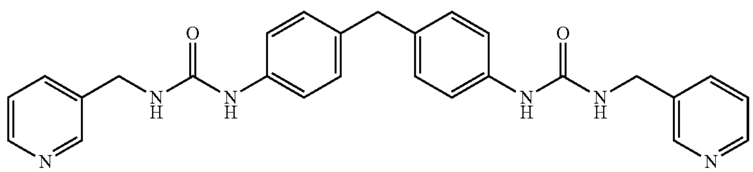 [SMILES: O=C(NCc1cccnc1)Nc1ccc(Cc2ccc(NC(=O)NCc3cccnc3)cc2)cc1] | 1.5 |
| 1,1'-(methylenebis(4,1-phenylene))bis(3-(pyridin-2-ylmethyl)urea) | 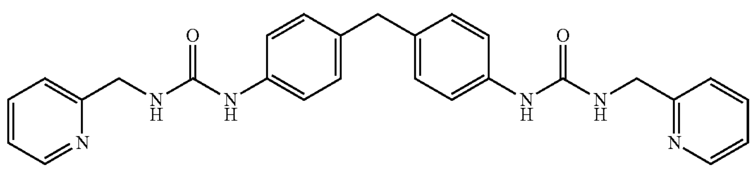 [SMILES: O=C(NCc1ccccn1)Nc1ccc(Cc2ccc(NC(=O)NCc3ccccn3)cc2)cc1] | 1.5 |

| IUPAC NAME | STRUCTURE (comparative) | MGC (% w/w) |
|---|---|---|
| N,N'-(2S,2'S)-1,1'-(dodecane-1,12-diylbis(azanediyl))bis(3-methyl-1-oxobutane-2,1-diyl)diisonicotinamide | | 0.4 |
| 1,1'-(dodecane-1,12-diyl)bis(3-(pyridin-4-ylmethyl)urea) | | 0.25 |

Comparison between urea analog of amino acid based gellant: the urea gellant is more efficient having a lower MGC in the same formula The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A urea gellant which is 1,1'-(dodecane-1,12-diyl)bis(3-(pyridin-4-ylmethyl)urea).

2. A liquid detergent composition comprising a surfactant and a urea gellant according to claim 1.

* * * * *